United States Patent [19]

Wehrmeister

[11] 4,071,520
[45] Jan. 31, 1978

[54] METHOD FOR PREPARING CARBOSTYRIL DERIVATIVES

[75] Inventor: Herbert Louis Wehrmeister, Terre Haute, Ind.

[73] Assignee: IMC Chemical Group, Inc., Terre Haute, Ind.

[21] Appl. No.: 689,400

[22] Filed: May 24, 1976

Related U.S. Application Data

[62] Division of Ser. No. 602,602, Aug. 6, 1975, Pat. No. 4,006,148.

[51] Int. Cl.$^2$ ............................................. C07D 215/22
[52] U.S. Cl. ............................ 260/287 K; 260/288 R; 260/289 K

[58] Field of Search ........... 260/289 K, 287 K, 288 R

[56] References Cited
PUBLICATIONS

Wehrmeister, J. Org. Chem., vol. 27, pp. 4418–4420 (1962).

Primary Examiner—Paul M. Coughlan, Jr.
Attorney, Agent, or Firm—Robert H. Dewey; Howard E. Post

[57] ABSTRACT

Carbostyril derivatives useful as coccidiostats are prepared by reacting an ortho-halo benzaldehyde with a 2-alkyl-2-oxazoline, then heating at above about 200° C thereby forming the carbostyril.

11 Claims, No Drawings

METHOD FOR PREPARING CARBOSTYRIL DERIVATIVES

This is a division of copending application Ser. No. 602,602 filed Aug. 6, 1975, U.S. Pat. No. 4,006,148.

BACKGROUND OF THE INVENTION

This invention relates to carbostyril derivatives. In a particular aspect, this invention relates to carbostyril derivatives having utility as coccidiostats.

Coccidiosis is a severe disease of poultry, especially chickens, and many compounds have been developed for combatting it. However, the causative organisms have the ability to develop resistance to such compounds to that after a period of use, most coccidiostats gradually lose their effectiveness and must be replaced. Accordingly there is a continuing need for new, non-toxic coccidiostats.

SUMMARY OF THE INVENTION

It is an object of this invention to provide novel carbostyril derivatives.

It is another object of this invention to provide carbostyril derivatives having coccidiostat activity.

Other objects of this invention will be apparent to those skilled in the art.

It is the discovery of this invention to provide a novel process for the preparation of carbostyril derivatives represented by formula I by reacting an o-haloaromatic aldehyde with a 2-substituted oxazoline:

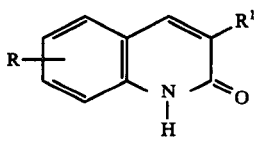

R can be chloro, nitro, or dimethylamino and $R^1$ can be hydrogen, alkyl, e.g. methyl, phenyl, p-methoxyphenyl, benzamido, 2,4-dichlorophenoxy or acetamido. These carbostyrils can be readily converted to the corresponding 2-chloroquinolines if desired.

DETAILED DISCUSSION

According to the process of the present invention, an o-haloaromatic aldehyde represented by formula II:

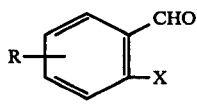

is reacted in a 1:1 mole ratio with an oxazoline represented by formula III:

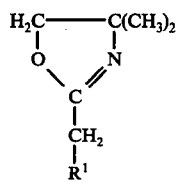

R and $R^1$ have the same meaning described above and X is a halogen atom, e.g. chloro- or bromo-.

The reactants are heated, preferably but not necessarily, in the presence of an acidic catalyst, e.g. sodium bisulfate, in a suitable solvent, e.g. a mixture of xylene or toluene with N-methylpyrrolidinone, dimethylformamide, decalin or tetralin, at reflux temperature. One mole of water is eliminated per mole of reactants, and when water stops coming off, the mixture is further heated to remove the xylene and refluxing is continued at 200°–300°, generally for from 15 min. to about 2 hours. One mole equivalent of methallyl chloride is a by-product of the reaction and collects in the distillate. After the reaction is complete, the mixture is cooled and poured into water whereupon the carbostyril product crystallizes. It is separated, e.g. by filtration, decantation or centrifugation, washed and dried. It can be recrystallized from acetic acid if further purification is desired.

It is known from H. L. Wehrmeister, J. Org. Chem. 27 4418 (1962), which is incorporated herein by reference thereto, that aromatic aldehydes react with 2-substituted-2-oxazolines to yield phenylethenyloxazolines. It is believed that such compounds are formed as intermediates in the present process during the water-elimination stage. Accordingly, it is another embodiment of the present invention to prepare the carbostyril derivatives by heating a phenylethenyloxazoline represented by the formula IV:

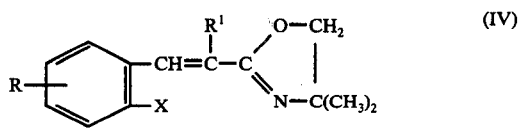

at 200°–220° C for a period of time sufficient to form a carbostyril derivative.

The carbostyrils of the present invention can be further reacted with phosphorous oxychloride to form chloroquinoline derivatives. Accordingly, it is another embodiment of the present invention to provide a novel process for the preparation of chloroquinoline derivatives.

Some of the compounds formed by the process of the present invention possess utility as coccidiostats. They are administered to poultry by incorporating them in the poultry feed at a concentration of about 200 g/ton. The effective compounds are represented by formula I wherein R is 5- or 7-chloro or 7-dimethylamino, and $R^1$ is hydrogen, methyl, acetamido, phenyl, p-methoxyphenyl or 2,4-dichlorophenoxy except that when R is 7-chloro, $R^1$ cannot be hydrogen. More particularly, there are preferred those compounds wherein R is 5- or 7-chloro and $R^1$ is hydrogen or phenyl and their corresponding quinolines. The especially preferred compounds include but are not limited to:

P-1983—2,7-dichloro-3-phenylquinoline
P-1995—2,5-dichloroquinoline
P-2000—7-chloro-3-phenylcarbostyril
P-2001—5-chlorocarbostyril The invention will be better understood with reference to the following examples. It is understood that the examples are intended only for purposes of illustrating the invention and it is not intended that the invention be limited thereby.

EXAMPLE 1

A stirred mixture of 2-benzyl-4,4-dimethyl-2-oxazoline (18.9 g., 0.1 mole), 2,4-dichlorobenzaldehyde (17.5 g., 0.1 mole) and 1 g. of sodium bisulfate in 50 ml. of N-methylpyrrolidinone and 30 ml. of xylene was heated at reflux under a short column, water separator (20 ml.), and condenser. Distillation to the separator occurred at a pot temperature of 177°–199° C. A total of 18 ml. of distillate was then drained from the separator intermittently during 1.25 hours with the pot temperature ultimately reaching 218°. Refluxing near 218° was continued an additional 15 minutes. The reaction mixture was cooled, then diluted with 300 ml. of water and filtered. The solid product was washed with 2 × 100 ml. water and 2 × 50 ml. of methanol and dried in a vacuum desiccator. There was obtained 21.4 g. (84%) of 7-chloro-3-phenylcarbostyril, m.p. 252°–253°. Recrystallization from 200 ml. of acetic acid gave 15.1 g., m.p. 252°–255°.

Analysis Calcd. for $C_{15}H_{10}ClNO$: C, 70.45; H, 3.94; Cl, 13.87; N, 5.48. Found: C, 70.36; H, 3.73; Cl, 13.60; N, 5.51.

The compound (P-2000) was used to combat coccidiosis in chicks. Chick starter rations were prepared according to the following formula:

| INGREDIENTS | |
| --- | --- |
| Ground yellow corn | 52.5% |
| Soybean meal 44% | 39.0% |
| Deh. alfalfa meal 17% | 2.5% |
| Corn oil | 3.0% |
| Salt | .5% |
| $CaCo_3$ | 1.0% |
| Dical, 24% Ca 21%P | 2.0% |
| DL-Methionine | .1% |
| Trace mineral mix | .05% |
| Vitamin premix | .25% |
| Calculated Analysis | |
| Protein % | 22.0 |
| *Me kcal/lb | 1400 |
| Calcium % | 1.0 |
| Phosp. total % | .80 |
| Avail. % | .54 |

*metabolizeable energy

A group of 20 broiler chicks, 2 weeks old, of mixed sex were chosen for the experiment. Half of them were controls, fed the above ration, and half were fed the above rations plus 200 g/ton of 7-chloro-3-phenylcarbostyril. On the second day of the test, each bird was orally inoculated with 1 cc of sporulated oocysts of Eimeria tenella containing approximately 100,000 oocysts per 1 cc. The results are given in Table 1.

Table 1

| | Untreated | Treated |
| --- | --- | --- |
| Morbidity at 6 days, % | 100 | 100 |
| Total bloody droppings | 158 | 91 |
| Total mortality | 5/10 | 1/10 |
| Av. body weight gain | 108 g/bird | 54 g/bird |

It was concluded that the compound is effective for combatting coccidiosis when present in the feed at a concentration of about 200 g/ton.

EXAMPLE 2

A stirred mixture of 5.0 g. of 7-chloro-3phenylcarbostyril (P-2000, prepared according to Example 1) and 25 ml. of $POCl_3$ was heated at reflux for 3 hours and then evaporated on a rotary evaporator finally at 90°, 20 mm. The residue in 200 ml. benzene was washed with 150 ml. 3% (w/v) aqueous sodium bicarbonate solution, dried with anhydrous $Na_2SO_4$, and evaporated to yield 5.3 g. of product, m.p. 99°–100° C. Recrystallization from hexane-benzene gave 4.1 g. of 2,7-dichloro-3-phenylquinoline, P-1983, m.p. 102°–103°. The elemental analyses are given in Table 4.

The product was used to combat coccidiosis in chicks following the same procedure as described in Example 1. The results are given in Table 2.

Table 2

| | Controls | Treated |
| --- | --- | --- |
| Morbidity at 6 days, % | 100 | 50 |
| Total bloody droppings | 100 | 33 |
| Total mortality | 6/10 | 2/10 |
| Postmortem lesions | 6/6 | 2/2 |
| Av. body weight gain | — | 119 g/bird |

It was concluded that P-1983 is effective for combatting coccidiosis when present in the feed at a concentration of about 200 g/ton

EXAMPLES 3–8

The experiment of Example 1 was repeated in all essential details except that the values for R and $R^1$ in the aldehydes and the oxazolines employed were selected as follows:

Table 3

| Example No. | Aldehyde R | Oxazoline $R^1$ |
| --- | --- | --- |
| 3 | 5-Cl | H |
| 4 | 5-Cl | Ph |
| 5 | 6-$NO_2$ | Ph |
| 6 | $(CH_3)_2N$ | Ph |
| 7 | 7-Cl | p-MeOPh* |
| 8 | 7-Cl | 2,4-$Cl_2$PhO** |

*p-methoxyphenyl
**2,4-dichlorophenoxy

The compounds obtained are listed in Table 4.

Compounds P-2001 and P-1999 were tested as coccidostats following the procedure of Example 1. Of the chicks receiving P-2001, there were six survivors out of ten. The morbidity was 50% and there were 72 bloody droppings. The weight gain averaged 125 g/chick. Compound P-2001 was concluded to be useful in combatting cocidiosis.

Compound P-1999 was ineffective.

The coccidiostat test described in Example 1 is repeated four times except that P-2000 is omitted and there is substituted therefor P-2007, P-2011, P-2012, and P-2015 respectively. Treated chicks infected with the coccidiosis-producing organism show a significant survival rate. It is concluded that each of the compounds is useful as a coccidiostat.

EXAMPLE 9

2-Acetamidomethyl-4,4-dimethyl-2-oxazoline was obtained by reacting N-acetylglycine with 2-amino-2-methyl-1-propanol. The oxazoline was then reacted with 2,4-dichlorobenzaldehyde in accordance with the experiment of Example 1. The resulting compound, 3-acetamido-7-chlorocarbostyril (P-2014) is listed in Table 4.

The coccidiostat test described in Example 1 is repeated in all essential details except that P-2014 is substituted for P-2000. Treated chicks infected with the coccidiosis-producing organism show a significant survival rate. It is concluded that each of the compounds is useful as a coccidiostat.

Table 4

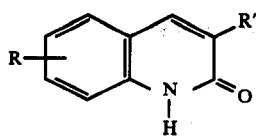

| Ex. No. | R | R' | Code No. | Yield % | m.p. °C | Formula | Calcd. C | Calcd. H | Calcd. N | Calcd. Cl | Found C | Found H | Found N | Found Cl |
|---|---|---|---|---|---|---|---|---|---|---|---|---|---|---|
| 3 | 5-Cl | H | P-2001 | 21 | 289-291 | C₉H₆ClNO | 60.18 | 3.37 | 7.80 | 19.74 | 60.00 | 3.17 | 7.67 | 19.20 |
| 4 | 5-Cl | Ph | P-2011 | 91 | 261.5-262.5 | C₁₅H₁₀ClNO | 70.45 | 3.94 | 5.48 | 13.87 | 70.53 | 3.97 | 5.32 | 13.43 |
| 5 | 6-NO₂ | Ph | P-1999 | 95 | 299-302 | C₁₅H₁₀N₂O₃ | 67.65 | 3.79 | 10.52 | — | 67.33 | 3.88 | 10.04 | — |
| 6 | 7-(CH₃)₂N | Ph | P-2012 | 33 | 249-255 | C₁₇H₁₆N₂O | 77.24 | 6.10 | 10.60 | — | 76.73 | 6.02 | 10.78 | — |
| 7 | 7-Cl | p-MeOPh | P-2007 | 67 | 261-263 | C₁₆H₁₂ClNO₂ | 67.26 | 4.24 | 4.90 | 12.41 | 66.92 | 4.09 | 4.87 | 12.54 |
| 8 | 7-Cl | 2,4-Cl₂PhO | P-2015 | 19 | 290-291 | C₁₅H₈Cl₃NO₂ | 52.89 | 2.37 | 4.11 | 31.23 | 52.65 | 2.30 | 3.96 | 31.09 |
| 9 | 7-Cl | O‖CH₃C—NH | P-2014 | 36 | 325-338 | C₁₁H₉ClN₂O₂ | 55.82 | 3.83 | 11.84 | 14.98 | 55.16 | 4.03 | 11.49 | 14.56 |

EXAMPLE 10

3-Methylcarbostyril (P-2018) is a known compound (F. Effenberger and W. Hartmann, Chem. Ber., 102, 3260 (1969)). It was prepared from 2-[2-(2-chlorophenyl)-1 methyl-ethenyl]-4,4-dimethyl-2-oxazoline by heating the oxazoline at 194°-268° C for 1.5 hours. The residue was crystallized from ethanol. Recrystallized product had a melting point of 240°-241° compared with the literature value of 238° in accordance with the procedure of Example 1.

A 5 g. portion was heated at reflux in 25 ml of POCl₃ for 3 hours. The resulting solution was diluted with 5-10 ml of toluene and evaporated on a rotary evapoator at water pump pressure. To the residue was added 25 ml of toluene and again evaporated. The residue was extracted with 2 × 50 ml of hot chloroform which, on evaporation, gave 5.6 q. residue which was crystallized from 22 ml of methanol to yield 1.2 g. of 2-chloro-3-phenyl-quinoline, P-1996, m.p. 56–56.5°.

Analysis: Calculated for C₁₅H₁₀ClN: C, 75.16; H, 4.21; Cl, 14.79; N, 5.84. Found: C, 75.21' H, 4.51; Cl, 14.79; N, 5.36. The infra-red absorption spectrum was consistent with the expected structure.

EXAMPLES 11-14

The experiment of Example 10 was repeated four times in all essential details except that in place of 3-methyl-carbostyril there was substituted, respectively, the carbostyrils of Examples 3, 4, 5 and 7. The resulting quinolines thereby obtained (Table 5) were:

Example 11—2,5-Dichloroquinoline (P-1995) from P-2001.

Example 12—2,5-Dichloro-3-phenylquinoline (P-1997) from P-2011.

Example 13—2-Chloro-6-nitro-3-phenylquinoline (P-1998) from P-1999.

Example 14—2,7-Dichloro-3-p-methoxyphenyl-quinoline (P-2002) from P-2007.

These compounds were tested as coccidiostats at 200 g/ton of feed by the procedure described in Example 1. Of 10 chicks receiving P-1995, all birds survived. There were 158 bloody droppings with a morbidity of 70%. The gain in weight averaged 119 g. per bird. It was concluded that P-1995 was useful as a coccidiostat, P-1997, P-1998 and P-2002 were ineffective as coccidiostats.

Table 5

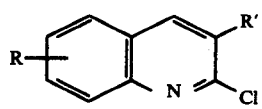

| Ex. No. | R | R' | Code No. | m.p. °C | Formula | Calcd. C | Calcd. H | Calcd. N | Calcd. Cl | Found C | Found H | Found N | Found Cl |
|---|---|---|---|---|---|---|---|---|---|---|---|---|---|
| 2 | 7-Cl | Ph | P-1983 | 102–103 | C₁₅H₉Cl₂N | 65.72 | 3.31 | 5.11 | 25.87 | 65.70 | 3.26 | 5.05 | 26.14 |
| 11 | 5-Cl | H | P-1995 | 78 – 78.5 | C₉H₅Cl₂N | 54.58 | 2.54 | 7.07 | 35.80 | 54.91 | 2.69 | 7.02 | 35.64 |
| 12 | 5-Cl | Ph | P-1997 | 133 – 134 | C₁₅H₉Cl₂N | 65.72 | 3.31 | 5.11 | 25.87 | 65.22 | 3.26 | 5.29 | 25.34 |
| 13 | 6-NO₂ | Ph | P-1998 | 212 – 212.5 | C₁₅H₉ClN₂O₂ | 63.28 | 3.19 | 9.84 | 12.46 | 63.37 | 3.30 | 9.47 | 11.59 |
| 14 | 7-Cl | p-MeOPh | P-2002 | 126 – 127.5 | C₁₆H₁₁Cl₂NO | 63.18 | 3.65 | 4.61 | 23.31 | 63.48 | 3.58 | 4.47 | 23.03 |

EXAMPLE 15

2-[2-(2,4-Dichlorophenyl)-1-methylethenyl]-4,4-dimethyl-2-oxazoline (P-2016) was prepared by reacting 2,4-dichlorobenzaldehyde with 4,4-dimethyl-2-ethyl-2-oxazoline in the presence of iodine catalyst.

P-2016, 40 g., was heated under nitrogen at 205°-295° for 2 hours while collecting the distillate. The residue was crystallized from 850 ml. of hot methanol to yield 10.5 g. of 7-chloro-3-methyl carbostyril, m.p. 240°-241°. It was designated P-2008. Methallyl chloride was identified in the distillate.

P-2008 is tested for coccidiostat activity according to the procedure described in Example 1. Treated chicks infected with the coccidiosis-producing organism show a significant survival rate, indicating that P-2008 is a useful coccidiostat.

EXAMPLE 16

The experiment of Example 1 was repeated in all essential details except that 2-bromobenzaldehyde was substituted for 2,4-dichlorobenzaldehyde on a mole for mole basis. There was obtained 3-phenylcarbostyril, a known compound, in 31% yield.

I claim:

1. A method for preparing carbostyril derivatives represented by the formula:

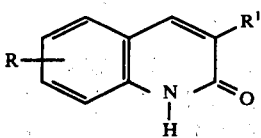

where R is 5 or 7-chloro, or 7-dimethylamino and $R^1$ is hydrogen, methyl, phenyl, p-methoxyphenyl, acetamido or 2,4-dichlorophenoxy with the proviso that when R is 7-chloro, $R^1$ cannot be hydrogen comprising the step of heating at 200°-220° C a phenylethenyl oxazoline represented by the formula

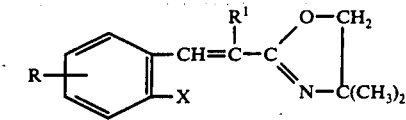

wherein X is a chlorine or bromine atom and R and $R^1$ have the same meanings defined above until said carbostyril derivative is formed.

2. The method of claim 1 wherein R is chloro.
3. The method of claim 1 wherein R is dimethylamino.
4. The method of claim 1 wherein $R^1$ is hydrogen.
5. The method of claim 1 wherein $R^1$ is methyl.
6. The method of claim 1 wherein $R^1$ is phenyl.
7. The method of claim 1 wherein $R^1$ is p-methoxyphenyl.
8. The method of claim 1 wherein $R^1$ is acetamido.
9. The method of claim 1 wherein $R^1$ is 2,4-dichlorophenoxy.
10. The method of claim 1 wherein X is chlorine.
11. The method of claim 1 wherein X is bromine.

UNITED STATES PATENT AND TRADEMARK OFFICE
CERTIFICATE OF CORRECTION

PATENT NO. : 4,071,520
DATED : January 31, 1978
INVENTOR(S) : Herbert Louis Wehrmeister It is certified that error appears in the above-identified patent and that said Letters Patent are hereby corrected as shown below:

Column 1, line 15, "to" should read -- so --

Column 4, line 43, "cocidiosis" should read -- coccidiosis --

Column 5, line 47, "evapoa-tor" should read -- evaporator --

Column 5, line 51, "5.6q." should read -- 5.6g. --

Signed and Sealed this

Eleventh Day of July 1978

[SEAL]

Attest:

RUTH C. MASON
Attesting Officer

DONALD W. BANNER
Commissioner of Patents and Trademarks